United States Patent
Iwatani

(10) Patent No.: US 12,194,121 B2
(45) Date of Patent: Jan. 14, 2025

(54) AQUEOUS EYEBROW COSMETIC AND EYEBROW COSMETIC PRODUCT

(71) Applicant: TOKIWA CORPORATION, Nakatsugawa (JP)

(72) Inventor: Yuko Iwatani, Kawaguchi (JP)

(*) Notice: Subject to any disclaimer, the term of this patent is extended or adjusted under 35 U.S.C. 154(b) by 200 days.

(21) Appl. No.: 17/933,483

(22) Filed: Sep. 20, 2022

(65) Prior Publication Data
US 2023/0190596 A1    Jun. 22, 2023

(30) Foreign Application Priority Data

Dec. 22, 2021 (JP) ................................ 2021-208427

(51) Int. Cl.
| | |
|---|---|
| *A61K 8/06* | (2006.01) |
| *A61K 8/00* | (2006.01) |
| *A61K 8/25* | (2006.01) |
| *A61Q 1/10* | (2006.01) |

(52) U.S. Cl.
CPC ............. *A61K 8/25* (2013.01); *A61K 8/06* (2013.01); *A61Q 1/10* (2013.01); *A61K 2800/43* (2013.01)

(58) Field of Classification Search
CPC ... A61Q 1/10; A61Q 5/00; A61Q 5/06; A61Q 1/00; A61K 8/8152; A61K 8/06; A61K 8/00; A61K 2800/10; A61K 8/04
See application file for complete search history.

(56) References Cited

U.S. PATENT DOCUMENTS

| | | | | |
|---|---|---|---|---|
| 2010/0031969 A1* | 2/2010 | Jager Lezer | ......... | A45D 40/262 424/70.17 |
| 2010/0267627 A1* | 10/2010 | Yagi | ......................... | A61P 3/10 435/375 |

FOREIGN PATENT DOCUMENTS

| | | | | |
|---|---|---|---|---|
| JP | H10-287523 | 10/1998 | | |
| WO | WO-2014062334 A1 * | 4/2014 | ........... | A61K 8/0241 |

OTHER PUBLICATIONS

Kunimine Industries Co., LTD. Pure Sodium Montmorillonite: Kunipia. Date retrieved: Jun. 8, 2023. < https://www.kunimine.co.jp/english/kaseihin/kasei_01.htm>. (Year: 2023).*

* cited by examiner

*Primary Examiner* — Tracy Liu
(74) *Attorney, Agent, or Firm* — SOEI PATENT & LAW FIRM

(57) ABSTRACT

An aqueous eyebrow cosmetic includes a clay mineral, a film-forming polymer emulsion, and water, in which the content of the clay material is 5 to 20% by mass based on the total amount of the aqueous eyebrow cosmetic, the film-forming polymer emulsion includes a polymer having a glass transition temperature of −20° C. or higher, and the content of the water is 30% by mass or greater based on the total amount of the aqueous eyebrow cosmetic.

18 Claims, No Drawings

AQUEOUS EYEBROW COSMETIC AND EYEBROW COSMETIC PRODUCT

CROSS-REFERENCE TO RELATED APPLICATIONS

This application claims the benefit of priority from Japanese Patent Application No. 2021-208427, filed on Dec. 22, 2021, the entire contents of which are incorporated herein by reference.

TECHNICAL FIELD

The present invention relates to an aqueous eyebrow cosmetic and an eyebrow cosmetic product.

BACKGROUND

For eyebrow makeup, coloring that changes the color of the eyebrows, styling such as adjusting the flow of the eyebrows, and increasing the volume of the eyebrows are performed. Liquid or gel eyebrow cosmetics are generally used for such makeup: coloring and styling can be performed by applying cosmetics to the eyebrows using an applicator having a coil-shaped (screw-shaped) or comb-shaped body.

Water-based liquid or gel eyebrow cosmetics are frequently used as liquid or gel eyebrow cosmetics, from the viewpoint of a quick drying property, and a film-forming agent such as an aqueous polymer is blended therein as a component that gives a styling effect (see, for example, Japanese Unexamined Patent Publication No. H10-287523).

SUMMARY

In recent years, eyebrow makeup has diversified. For example, known makeup raises the eyebrows to stand upright using a technique such as soap brows. Such makeup requires a power (setting power) for fixing the eyebrows in a standing upright state and a power (keeping power) for maintaining the fixed state.

However, eyebrow cosmetics, which can achieve a natural finish while satisfying the aforementioned requirements, have not been realized. Conventional eyebrow cosmetics find a difficulty in gaining the setting power and the keeping power required for the aforementioned makeup. When trying to increase the setting power and the keeping power, the quick drying property tends to be impaired and the natural finish tends to be difficult to achieve. For example, with an aqueous cosmetic in which a large amount of a film-forming agent such as an aqueous polymer is blended, it is likely that stickiness will be felt between application and drying and a stiff feeling will become stronger after drying. Moreover, if combing is repeated with a comb-shaped applicator during the setting process, flaking that makes the eyebrows whitish occurs and the eyebrows are fixed in a bundle, which likely causes an unnatural finish.

Disclosed herein are an aqueous eyebrow cosmetic and an eyebrow cosmetic product that are configured to have an excellent quick drying property and achieve a natural finish while having a setting power and a keeping power which can maintain a state where the eyebrows stand upright.

In some examples, an aqueous eyebrow cosmetic comprises (A) a clay mineral, (B) a film-forming polymer emulsion, and (C) water, in which the content of the (A) component is 5 to 20% by mass based on the total amount of the aqueous eyebrow cosmetic, the (B) component comprises a polymer having a glass transition temperature of −20° C. or higher, and the content of the (C) component is 30% by mass or greater based on the total amount of the aqueous eyebrow cosmetic.

With the aforementioned configuration, the aqueous eyebrow cosmetic can have an excellent quick drying property while having a setting power and a keeping power which can maintain a state where the eyebrows stand upright, can prevent the eyebrows from becoming whitish or sticking to each other when using an applicator, and can achieve a natural finish.

It may be inferred that when an aqueous cosmetic comprising a specific film-forming polymer emulsion is blended with a specific amount of a clay mineral, water is quickly released through the clay mineral at the time of application, a coating film is dried without stickiness, and thus a high setting power and a high keeping power can be obtained while suppressing the stiffness, whitening, and bundle-form fixation of the eyebrows caused by the film-forming agent as described above. This rational may account for the obtained effects.

One of the eyebrow makeup methods is that coloring and styling may be performed by using a pencil-type eyebrow cosmetic, such as an eyebrow pencil, and a liquid or gel eyebrow cosmetic having a styling effect in combination. In this case, in order to prevent the styling from degrading, an eyebrow cosmetic was applied to the eyebrows after using the eyebrow pencil. According to the aqueous eyebrow cosmetic, the eyebrows can be finished flexibly with a high setting power, and thus the styling is less likely to degrade even if drawing with the pencil-type eyebrow cosmetic is performed on the styled eyebrows. Accordingly, the aqueous eyebrow cosmetic can be used regardless of the order of makeup, and thus also has an advantage that the finish of eyebrow makeup can be easily adjusted.

In some examples, the aqueous eyebrow cosmetic may comprise, as the (A) component, (A1) a clay mineral having a viscosity of 5,000 mPa·s or greater as measured at 25° C. when made into a 4% by mass aqueous solution, and the content of the (A1) component may be 10% by mass or greater based on the total amount of the (A) component.

In some examples, the content of the (B) component may be 0.3 to 5.0% by mass, in terms of solid content, based on the total amount of the aqueous eyebrow cosmetic.

In some examples, the mass ratio of the content of the (A) component to the content of the (B) component in terms of solid content may be 1.8 or greater.

In some examples, an eyebrow cosmetic product comprises: the aqueous eyebrow cosmetic housed in a container; and an applicator having a coil-shaped or comb-shaped body.

DETAILED DESCRIPTION

Before addressing details of example embodiments described below, some terms are defined or clarified.

As may be used herein, the terms "comprises," "comprising," "includes," "including," "has," "having" or any other variation thereof, are intended to cover a non-exclusive inclusion. For example, a composition that comprises a list of elements is not necessarily limited to only those elements but may include other elements not expressly listed or inherent to such composition.

Unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed provided that these additional included materials, steps, features, components, or elements do materially affect the basic and novel characteristic(s) of the claimed invention. The term 'consisting essentially of' occupies a middle ground between "comprising" and 'consisting of'.

Where applicants have defined an invention or a portion thereof with an open-ended term such as "comprising," it should be readily understood that (unless otherwise stated) the description should be interpreted to also describe such an invention using the terms "consisting essentially of" or "consisting of."

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

An example aqueous eyebrow cosmetic comprises (A) a clay mineral (hereinafter, may be referred to as an (A) component), (B) a film-forming polymer emulsion (hereinafter, may be referred to as a (B) component) comprising a polymer having a glass transition temperature of −20° C. or higher, and (C) water (hereinafter, may be referred to as a (C) component).

The (A) component to be used may be a mineral such as hydrous silicate, layered silicate, or hydrous layered silicate. The (A) component may also be a natural product or a synthetic product that is used in ordinary cosmetics.

The (A) component may be a clay mineral of the smectite group such as hectorite, saponite, stevensite, hyderite, montmorillonite, nontronite, or bentonite, or a clay mineral of the kaolin group such as kaolinite.

The (A) component to be used may be a purified product or a synthetic product from the viewpoint of containing few impurities, and for example, synthetic smectite, purified bentonite, and the like can be used. Use of such clay minerals will easily enhance the transparency of cosmetics.

The synthetic smectite to be used may be fluorine hectorite, hectorite, saponite, or stevensite. These substances are designated by names such as silicic acid (Al/Mg), silicic acid (Na/Mg), silicic acid (Li/Mg/Na), and quaternium-18 hectorite.

The (A) component may employ a commercially available product such as SUMECTON and KUNIPIA (both produced by KUNIMINE INDUSTRIES CO., LTD., trade names), LAPONITE (produced by Rockwood Additives Ltd., trade name), or ASP (produced by BASF SE, trade name).

The aqueous eyebrow cosmetic may comprise, as the (A) component, (A1) a clay mineral having a viscosity of 5,000 mPa·s or greater as measured at 25° C. when dispersed at a concentration of 4% by mass in water, from the viewpoint of improving the setting power. The aqueous eyebrow cosmetic may comprise, as the (A) component, (A2) a clay mineral having a viscosity of 1 mPa·s or greater and less than 5,000 mPa·s as measured at 25° C. when dispersed at a concentration of 4% by mass in water, from the viewpoints of further suppressing stickiness, achieving the natural finish, and further improving the keeping power.

The viscosity refers to a value measured under the conditions described below for a sample at 25° C. obtained by stirring and dispersing a clay mineral at a concentration of 4% by mass in water and leaving the resultant for 24 hours.
Viscometer: Brookfield-Type Viscometer (BM Type)
  5 to 50 mPa·s: BL adapter with a rotation speed of 12 rpm
  50 to 500 mPa·s: Rotor No. 1 with a rotation speed of 12 rpm
  200 to 2,500 mPa·s: Rotor No. 2 with a rotation speed of 12 rpm
  1,000 to 10,000 mPa-s: Rotor No. 3 with a rotation speed of 12 rpm
  10,000 mPa·s or greater: BH adapter, rotor No. 6 with a rotation speed of 10 rpm The aqueous eyebrow cosmetic may comprise, as the (A1) component, a clay mineral having a viscosity of 5,000 to 50,000 mPa·s, 5,500 to 40,000 mPa-s, or 6,000 to 30,000 mPa·s from the viewpoint of the setting power. The viscosity of the (A1) component may be 7,000 mPa·s or greater, 8,000 mPa·s or greater, 9,000 mPa·s or greater, 10,000 mPa·s or greater, 11,000 mPa·s or greater, 12,000 mPa·s or greater, 13,000 mPa·s or greater, 14,000 mPa·s or greater, 15,000 mPa·s or greater, 16,000 mPa·s or greater, 17,000 mPa·s or greater, 18,000 mPa·s or greater, or 19,000 mPa·s or greater, from the viewpoint of a setting power. The viscosity of the (A1) component may be 28,000 mPa·s or less, 27,000 mPa·s or less, 26,000 mPa·s or less, 25,000 mPa·s or less, 24,000 mPa·s or less, 23,000 mPa·s or less, 22,000 mPa·s or less, or 21,000 mPa·s or less, from the viewpoint of the setting power.

The (A1) component may be synthetic smectite from the viewpoint of less stickiness and the quick drying property.

The aqueous eyebrow cosmetic may comprise, as the (A2) component, a clay mineral having a viscosity of 1 to 4,500 mPa·s, a clay mineral having a viscosity of 50 to 4,000 mPa·s, or a clay mineral having a viscosity of 100 to 3,000 mPa·s, from the viewpoint of quick drying. The viscosity of the (A2) component may be 200 mPa·s or greater, 300 mPa·s or greater, 400 mPa·s or greater, 500 mPa·s or greater, 600 mPa·s or greater, 700 mPa·s or greater, 800 mPa·s or greater, 900 mPa·s or greater, 1,000 mPa·s or greater, 11,000 mPa·s or greater, or 12,000 mPa·s or greater. The viscosity of the (A2) component may be 2,500 mPa·s or less, 2,000 mPa·s or less, 1,500 mPa·s or less, or 1,400 mPa·s or less.

The (A2) component may be bentonite from the viewpoint of the natural finish and the quick drying property.

The content of the (A1) component may be 10% by mass or greater, 20% by mass or greater, 30% by mass or greater, 40% by mass or greater, 50% by mass or greater, 60% by mass or greater, 70% by mass or greater, 80% by mass or greater, or 85% by mass or greater, based on the total amount of the (A) component, from the viewpoint that the quick drying property and the natural finish are easily achieved.

The content of the (A2) component may be 0.1 to 20% by mass, 0.5 to 15% by mass, or 1 to 10% by mass, based on the total amount of the cosmetic.

One kind of the (A) component can be used alone, or two or more kinds thereof can be used in combination. Also, with respect to the (A1) component or the (A2) component, one kind thereof can be used alone, or two or more kinds thereof can be used in combination.

The aqueous eyebrow cosmetic may comprise the (A1) component and the (A2) component as the (A) component. In this case, the blending ratio (A1)/(A2) of the (A1) component to the (A2) component may be 1/100 to 100/1 from the viewpoint of making it easy to obtain non-sticky usability. The blending ratio may also be 1/9 to 100/1, 1/9 to 50/1, 1/9 to 10/1, 1/9 to 8/1, 1/9 to 5/1, 1/9 to 2/1, 3/7 to 100/1, 3/7 to 50/1, 3/7 to 10/1, 3/7 to 8/1, 3/7 to 5/1, 3/7 to 2/1, 4/7 to 100/1, 4/7 to 50/1, 4/7 to 10/1, 4/7 to 8/1, 4/7 to 5/1, 4/7 to 2/1, 1/1 to 100/1, 1/1 to 50/1, 1/1 to 10/1, 1/1 to 8/1, 1/1 to 5/1, or 1/1 to 2/1 from the viewpoint of the natural finish and the quick drying property.

The aqueous eyebrow cosmetic may comprise, as the (A) component, (A1-1) a clay mineral having a viscosity of 5,500 to 40,000 mPa·s and (A2-1) a clay mineral having a viscosity of 50 to 4,000 mPa·s in a mass ratio (A1-1)/(A2-1) of 1/1 to 10/1, or may comprise (A1-1) a clay mineral having a viscosity of 6,000 to 30,000 mPa·s and (A2-2) a clay mineral having a viscosity of 100 to 3,000 mPa·s in a mass ratio (A1-2)/(A2-2) of 1/1 to 10/1, from the viewpoint of the natural finish and the quick drying property.

The content of the (A) component in the aqueous eyebrow cosmetic may be 5 to 20% by mass, 5 to 18% by mass, 5 to 15% by mass, 5 to 10% by mass, 5 to 9% by mass, 5.5 to 20% by mass, 5.5 to 18% by mass, 5.5 to 15% by mass, 5.5 to 10% by mass, 5.5 to 9% by mass, 6 to 20% by mass, 6 to 18% by mass, 6 to 15% by mass, 6 to 10% by mass or 6 to 9% by mass, from the viewpoint of achieving sufficient setting and keeping powers, the quick drying property, and the natural finish.

Examples of the polymer contained in the (B) component include water-insoluble polymer and copolymer, each of which comprises an alkyl (meth)acrylate monomer as a constituent unit. Examples of the constituent unit of the copolymer include a vinyl acetate monomer and a styrene monomer. The copolymer may be any of a random copolymer, a graft copolymer, a block copolymer, and a core-shell-type copolymer.

Specific examples of the (B) component include an alkyl acrylate copolymer emulsion, an alkyl acrylate/styrene copolymer emulsion, and an alkyl acrylate/vinyl acetate copolymer emulsion. The alkyl acrylate referred to herein comprises alkyl methacrylate. The (B) component to be used may be a substance that uses water as medium and has a solid content concentration of 30 to 60% by mass.

The glass transition temperature of the polymer is –20° C. or higher from the viewpoint of achieving the sufficient setting and keeping powers, the quick drying property, and the natural finish. The glass transition temperature may also be –15° C. or higher, –14° C. or higher, –10° C. or higher, 0° C. or higher, 5° C. or higher, 10° C. or higher, 20° C. or higher, 25° C. or higher, 30° C. or higher, or 35° C. or higher, and may be 50° C. or lower, 45° C. or lower, or 40° C. or lower from the viewpoint of the natural finish and ease of drawing with a pencil after application. The glass transition temperature of the polymer is obtained through DSC measurement.

The emulsion particle diameter of the (B) component may be 10 to 150 nm, 10 to 130 nm, 10 to 110 nm, 10 to 100 nm, 10 to 90 nm, 10 to 80 nm, 10 to 70 nm, 10 to 65 nm, 20 to 150 nm, 20 to 130 nm, 20 to 110 nm, 20 to 100 nm, 20 to 90 nm, 20 to 80 nm, 20 to 70 nm, 20 to 65 nm, 30 to 150 nm, 30 to 130 nm, 30 to 110 nm, 30 to 100 nm, 30 to 90 nm, 30 to 80 nm, 30 to 70 nm, 30 to 65 nm, 40 to 150 nm, 40 to 130 nm, 40 to 110 nm, 40 to 100 nm, 40 to 90 nm, 40 to 80 nm, 40 to 70 nm, or 40 to 65 nm from the viewpoint of achieving the sufficient setting and keeping powers, the quick drying property, and the natural finish. When the emulsion particle diameter of the (B) component is 30 to 90 nm, whitening is less likely to occur even in the case where the aqueous eyebrow cosmetic is repeatedly applied. The emulsion particle diameter is measured by a dynamic light scattering-type particle size distribution meter (for example, LB-550 manufactured by HORIBA, Ltd.).

The (B) component may employ a commercially available product such as "DAITOSOL 3000SLPN," "DAITOSOL 3000VP3", "DAITOSOL 4000SJT," "DAITOSOL 5000AD" (all produced by DAITO KASEI KOGYO CO., LTD., trade names), "YODOSOL GH800" and "YODOSOL GH800F" (both produced by Akzo Nobel, trade names), or "COVACRYL MS11" (produced by Sensient Cosmetic Technologies, trade name).

One kind of the (B) component can be used alone, or two or more kinds thereof can be used in combination.

The content of the (B) component in the aqueous eyebrow cosmetic may be, in terms of a solid content concentration, 0.3 to 5.0% by mass, 0.5 to 4.0% by mass, or 1.0 to 3.0% by mass, based on the total amount of the cosmetic, from the viewpoint of achieving the sufficient setting and keeping powers, the quick drying property, and the natural finish.

In the aqueous eyebrow cosmetic, the mass ratio [(A)/(B)] of the content of the (A) component to the content of the (B) component in terms of solid content may be 1.8 or greater, 2.0 or greater, or 2.5 or greater, and may be 25 or less, 20 or less, or 16 or less.

The content of water, which is the (C) component, is 30% by mass or greater based on the total amount of the cosmetic. The content of water may be 40 to 90% by mass or 50 to 80% by mass from the viewpoint of the quick drying property.

The aqueous eyebrow cosmetic may further comprise at least one alcoholic medium, in addition to the water. The alcoholic medium may comprise a lower alcohol having 1 to 5 carbon atoms. The alcoholic medium may comprise a monool having one hydroxy group, polyol having two or more hydroxy group or a mixture thereof. Examples of the alcoholic medium include ethanol, 1,3-butylene glycol and a mixture thereof. The total content of alcoholic medium may be 1 to 15% by mass, 3 to 12% by mass or 5 to 10% by mass based on the total amount of the cosmetic. The content of the lower alcohol may be 1 to 10% by mass or 3 to 7% by mass based on the total amount of the cosmetic.

The aqueous eyebrow cosmetic may comprise a coloring material from the viewpoint of obtaining a coloring effect. Examples of the coloring material include a coloring pigment, a water-soluble dye, and a brilliant powder. One kind of the coloring material or two or more kinds thereof can be used.

Examples of the coloring pigment include inorganic coloring pigments such as red iron oxide, yellow iron oxide, black iron oxide, titanium oxide, carbon black, cobalt oxide, chromium oxide, ultramarine blue, Prussian blue, and zinc oxide, organic coloring pigments such as Red No. 228, Red No. 226, Blue No. 404, Red No. 202, and Yellow No. 4 aluminum lake, and natural colorants such as carmine. Examples of the water-soluble dye include organic dyes such as Red No. 227, Blue No. 1, Yellow No. 4, and Yellow No. 5, and natural colorants such as safflower. Examples of the brilliant powder include titanium oxide-coated mica (mica titanium), iron oxide-coated mica, iron oxide-coated mica titanium, organic pigment-coated mica titanium, a titanium oxide-coated glass powder, a titanium oxide and iron oxide-coated glass powder, and an aluminum powder.

The blending amount of the coloring material in the aqueous eyebrow cosmetic may be less than 1% by mass, less than 0.5% by mass, less than 0.2% by mass, or less than 0.1% by mass, based on the total amount of the cosmetic. In this case, the aqueous eyebrow cosmetic can be used as a transparent-type eyebrow styling agent. Moreover, according to the aqueous eyebrow cosmetic, the eyebrows can be finished flexibly with a high setting power, and thus the styling is less likely to degrade even if drawing with a pencil-type eyebrow cosmetic is performed on the styled eyebrows (in other words, ease of drawing with a pencil after application is excellent). Accordingly, coloring can be performed with an eyebrow pencil or the like, as needed, after styling.

The aqueous eyebrow cosmetic may comprise a fiber from the viewpoint of obtaining a volume-up effect. Examples of the fiber include a nylon fiber, a rayon fiber, a polypropylene fiber, a polyester fiber, and a cellulose fiber. The length of the fiber is not particularly limited. The length of the fiber may be 0.1 to 10 mm and may further be 0.3 to 7 mm. The thickness of the fiber may be 0.1 to 25 tex (hereinafter, simply referred to as "T") and may further be 0.3 to 20 T. The shape of the cross section of the fiber is not particularly limited. One kind or two or more kinds of these fibers having different materials, thicknesses, or lengths can be used.

In addition to the aforementioned components, other components, which are usually used in cosmetics, for example, a surfactant, a film-forming agent other than the (B) component, a powder component other than the aforementioned pigments and fibers, a moisturizing agent, a viscosity modifier, a preservative, a pH adjuster, a chelating agent, an ultraviolet ray absorber, vitamins, a beautifying component, an antioxidant, a flavoring agent, and the like can be appropriately blended, as needed, in the aqueous eyebrow cosmetic as long as the effects of the present invention are not impaired.

From the viewpoint of the quick drying property, the content of a polysaccharide thickener in the aqueous eyebrow cosmetic may be 1% by mass or less, 0.5% by mass or less, 0.3% by mass or less, or 0.1% by mass or less, based on the total amount of the cosmetic. The aqueous eyebrow cosmetic may not comprise the polysaccharide thickener. According to the aqueous eyebrow cosmetic, separation or precipitation can be sufficiently suppressed even when the polysaccharide thickener is not blended, and thus both quick drying property and storage stability can be achieved by limiting the blending amount of the polysaccharide thickener that tends to cause stickiness.

Since the aqueous eyebrow cosmetic has a sufficiently quick drying property, the content of volatile components (providing that water is excluded) may be 10% by mass or less, 7% by mass or less, or 5% by mass or less, based on the total amount of the cosmetic. The aqueous eyebrow cosmetic may not comprise the volatile component (providing that water is excluded).

The content of an oily component in the aqueous eyebrow cosmetic may be 5% by mass or less or 1% by mass or less from the viewpoint of storage stability.

The consistency of the aqueous eyebrow cosmetic may be 0.2 to 1.2 N or 0.3 to 0.9 N from the viewpoint of the setting power and the natural finish. The consistency of the cosmetic is obtained by the following measuring method.

Method for Measuring Consistency

A measurement sample is prepared by filling a screw cup having a capacity of 30 mL with a cosmetic and leaving the screw cup at 25° C. overnight (24 hours). The consistency of this measurement sample is measured at 25° C. using a FUDOH rheometer RT-2002D.D (manufactured by Rheotech Co., Ltd.) with a pressure-sensitive shaft of 10 φ sphere, a needle insertion speed of 6 cm/min, and a needle insertion depth of 10 mm.

The aqueous eyebrow cosmetic can be produced by dissolving or dispersing the aforementioned (A) component, (B) component, and (C) component, and, as needed, other components, and uniformly stirring and mixing these components. For example, a Disper can be used for the stirring and mixing.

Application of the aqueous eyebrow cosmetic using, for example, an applicator having a coil-shaped or comb-shaped body can obtain a styling effect and, as needed, a coloring effect and can make up the eyebrows. The aqueous eyebrow cosmetic can be used as an eyebrow gel or an eyebrow mascara.

An eyebrow cosmetic product may comprise: the aqueous eyebrow cosmetic housed in a container; and an applicator having a coil-shaped or comb-shaped body.

Examples of the coil-shaped or comb-shaped body include a winding brush, a comb, and a brush.

Hereinafter, details of additional example embodiments will be described with reference to comparative examples.

Production of Aqueous Eyebrow Cosmetic

Examples 1 to 19 and Comparative Examples 1 to 6

The respective components shown in Tables 1 to 4 were mixed with a Disper in the ratios (% by mass) shown in Tables 1 to 4 to obtain respective aqueous eyebrow cosmetics. The value of the polymer emulsion in the tables indicates the blending amount of the solid content. The "trace amount" in the tables refers to an amount of 1% by mass or less.

As the respective components shown in Tables 1 to 4, the following components were used.

Synthetic smectite-1: "SUMECTON SA" (trade name, produced by KUNIMINE INDUSTRIES CO., LTD., synthetic saponite with a viscosity of 20,500 mPa·s)

Synthetic smectite-2: "SUMECTON ST" (trade name, produced by KUNIMINE INDUSTRIES CO., LTD., synthetic stevensite with a viscosity of 6,650 mPa·s)

Bentonite-1: "KUNIPIA G" (trade name, produced by KUNIMINE INDUSTRIES CO., LTD., purified bentonite with a viscosity of 1,300 mPa·s)

Film-forming polymer emulsion-1: "DAITOSOL 3000SLPN" (trade name, produced by DAITO KASEI KOGYO CO., LTD., an acrylate copolymer with a Tg of 37° C. and an emulsion particle diameter of 50 nm)

Film-forming polymer emulsion-2: "DAITOSOL 3000VP3" (trade name, produced by DAITO KASEI KOGYO CO., LTD., an acrylate copolymer with a Tg of 25° C. and an emulsion particle diameter of 20 nm)

Film-forming polymer emulsion-3: "DAITOSOL 4000SJT" (trade name, produced by DAITO KASEI KOGYO CO., LTD., an acrylate/ethylhexyl acrylate copolymer with a Tg of −13° C. and an emulsion particle diameter of 60 nm)

Film-forming polymer emulsion-4: "DAITOSOL 5000AD" (trade name, produced by DAITO KASEI KOGYO CO., LTD., an acrylate copolymer with a Tg of −14° C. and an emulsion particle diameter of 140 nm)

Film-forming polymer emulsion-5: "DAITOSOL 5500GM" (trade name, produced by DAITO KASEI KOGYO CO., LTD., an acrylate/ethylhexyl acrylate copolymer with a Tg of −67° C. and an emulsion particle diameter of 160 nm)

PVP: PVP K-90 (trade name, produced by Ashland Specialty Ingredients, polyvinyl pyrrolidone)

The viscosity of the clay mineral was measured under the conditions described below for a sample at 25° C. obtained by stirring and dispersing a clay mineral at a concentration of 4% by mass in water and leaving the resultant for 24 hours.

Viscometer: Brookfield-type viscometer (BM type)
5 to 50 mPa·s: BL adapter with a rotation speed of 12 rpm
50 to 500 mPa·s: Rotor No. 1 with a rotation speed of 12 rpm
200 to 2,500 mPa·s: Rotor No. 2 with a rotation speed of 12 rpm
1,000 to 10,000 mPa·s: Rotor No. 3 with a rotation speed of 12 rpm
10,000 mPa·s or greater: BH adapter, rotor No. 6 with a rotation speed of 10 rpm Evaluation of Aqueous Eyebrow Cosmetics For the aqueous eyebrow cosmetics obtained above, the setting power, the quick drying property, the natural finish (item 1: no stiffness), the natural finish (item 2: no whitening and no eyebrows sticking to each other), the keeping power, and the ease of drawing with a pencil after application were evaluated according to the following evaluation method.

Evaluation Method

Five panelists with their eyebrows having a length of 1 cm or longer were asked to perform the use tests of the cosmetics of Examples and Comparative Examples and to evaluate from the viewpoint of the aforementioned evaluation items. In the use tests, the cosmetic was applied with a brush, and styling in which the eyebrows stand upright was performed. The item 2 of the natural finish and the ease of drawing with a pencil after application were evaluated after each cosmetic was filled in a mascara bottle, applied 20 times with a brush, and then completely dried. Regarding the keeping power, the condition of the eyebrows 2 hours after the application was evaluated.

In the evaluations, five-graded evaluation was performed according to the following evaluation criteria, a score was given to each sample, and the average score of the scores of all of the panelists was determined according to the following determination criteria.

[Score: Evaluation Criteria]
5 points: Very good
4 points: Good
3 points: Normal
2 points: Slightly poor
1 point: Poor

[Determination criteria (average score of scores)]
AA: 4 or more
A: 3 or more and less than 4
B: 2 or more and less than 3
C: Less than 2

Measurement of Consistency

A measurement sample was prepared by filling a screw cup having a capacity of 30 mL with the aqueous eyebrow cosmetic obtained above and leaving the screw cup at 25° C. overnight (24 hours). The consistency of this measurement sample was measured at 25° C. using a FUDOH rheometer RT-2002D.D (manufactured by Rheotech Co., Ltd.) with a pressure-sensitive shaft of 10 φ sphere, a needle insertion speed of 6 cm/min, and a needle insertion depth of 10 mm.

TABLE 1

|  |  |  | Example 1 | Example 2 | Example 3 | Example 4 | Example 5 | Example 6 |
|---|---|---|---|---|---|---|---|---|
| (A) | (A1) | Synthetic smectite-1 | 6 | 6 | 6 | 6 | 6 | 6 |
|  |  | Synthetic smectite-2 | — | — | — | — | — | — |
|  | (A2) | Bentonite-1 | — | — | — | — | — | — |
| (B) |  | Film-forming polymer emulsion-1 | 1.5 | — | — | — | 2.5 | 0.3 |
|  |  | Film-forming polymer emulsion-2 | — | 1.5 | — | — | — | — |
|  |  | Film-forming polymer emulsion-3 | — | — | 1.5 | — | — | — |
|  |  | Film-forming polymer emulsion-4 | — | — | — | 1.5 | — | — |
|  |  | Film-forming polymer emulsion-5 | — | — | — | — | — | — |
|  |  | PVP | — | — | — | — | — | — |
|  |  | Ethanol | 5 | 5 | 5 | 5 | 5 | 5 |
|  |  | 1,3-Butylene glycol | 3 | 3 | 3 | 3 | 3 | 3 |
|  |  | Preservative | Trace amount | Trace amount | Trace amount | Trace amount | Trace amount | Trace amount |
|  |  | pH adjuster | Trace amount | Trace amount | Trace amount | Trace amount | Trace amount | Trace amount |
| (C) |  | Purified water | Balance | Balance | Balance | Balance | Balance | Balance |
| Evaluation |  | Setting power | AA | AA | AA | AA | AA | AA |
|  |  | Quick drying property | AA | AA | AA | AA | AA | AA |
|  |  | Natural finish (item 1) | AA | AA | AA | AA | AA | AA |
|  |  | Natural finish (item 2) | AA | AA | AA | A | AA | AA |
|  |  | Keeping power | AA | AA | AA | AA | AA | A |
|  |  | Ease of drawing with pencil after application | AA | AA | AA | AA | AA | AA |
|  |  | Consistency (N) | 0.5 | 0.5 | 0.5 | 0.5 | 0.5 | 0.5 |

TABLE 2

|  |  |  | Example 7 | Example 8 | Example 9 | Example 10 | Example 11 | Example 12 |
|---|---|---|---|---|---|---|---|---|
| (A) | (A1) | Synthetic smectite-1 | 5 | 5 | 8 | 10 | — | — |
|  |  | Synthetic smectite-2 | — | — | — | — | 6 | 12 |
|  | (A2) | Bentonite-1 | — | — | — | — | — | — |
| (B) |  | Film-forming polymer emulsion-1 | 1.5 | 2.5 | 1.5 | 1.5 | 1.5 | 1.5 |
|  |  | Film-forming polymer emulsion-2 | — | — | — | — | — | — |
|  |  | Film-forming polymer emulsion-3 | — | — | — | — | — | — |

TABLE 2-continued

|  |  | Example 7 | Example 8 | Example 9 | Example 10 | Example 11 | Example 12 |
|---|---|---|---|---|---|---|---|
|  | Film-forming polymer emulsion-4 | — | — | — | — | — | — |
|  | Film-forming polymer emulsion-5 | — | — | — | — | — | — |
|  | PVP | — | — | — | — | — | — |
|  | Ethanol | 5 | 5 | 5 | 5 | 5 | 5 |
|  | 1,3-Butylene glycol | 3 | 3 | 3 | 3 | 3 | 3 |
|  | Preservative | Trace amount | Trace amount | Trace amount | Trace amount | Trace amount | Trace amount |
|  | pH adjuster | Trace amount | Trace amount | Trace amount | Trace amount | Trace amount | Trace amount |
| (C) | Purified water | Balance | Balance | Balance | Balance | Balance | Balance |
| Evaluation | Setting power | A | A | AA | AA | A | AA |
|  | Quick drying property | AA | AA | AA | AA | AA | AA |
|  | Natural finish (item 1) | AA | AA | AA | AA | AA | AA |
|  | Natural finish (item 2) | AA | AA | AA | AA | AA | AA |
|  | Keeping power | AA | AA | AA | AA | AA | AA |
|  | Ease of drawing with pencil after application | AA | AA | AA | AA | AA | AA |
|  | Consistency (N) | 0.3 | 0.3 | 0.8 | 1.1 | 0.2 | 0.8 |

TABLE 3

|  |  |  | Example 13 | Example 14 | Example 15 | Example 16 | Example 17 | Example 18 | Example 19 |
|---|---|---|---|---|---|---|---|---|---|
| (A) | (A1) | Synthetic smectite-1 | — | — | — | 3 | 5 | 9 | 4 |
|  |  | Synthetic smectite-2 | — | — | — | — | — | — | — |
|  | (A2) | Bentonite-1 | 12 | 12 | 9 | 7 | 5 | 1 | 4 |
| (B) |  | Film-forming polymer emulsion-1 | 1.5 | 4 | 5 | 1.5 | 1.5 | 1.5 | 4 |
|  |  | Film-forming polymer emulsion-2 | — | — | — | — | — | — | — |
|  |  | Film-forming polymer emulsion-3 | — | — | — | — | — | — | — |
|  |  | Film-forming polymer emulsion-4 | — | — | — | — | — | — | — |
|  |  | Film-forming polymer emulsion-5 | — | — | — | — | — | — | — |
|  |  | PVP | — | — | — | — | — | — | — |
|  |  | Ethanol | 5 | 5 | 5 | 5 | 5 | 5 | — |
|  |  | 1,3-Butylene glycol | 3 | 3 | 3 | 3 | 3 | 3 | 3 |
|  |  | Preservative | Trace amount | Trace amount | Trace amount | Trace amount | Trace amount | Trace amount | Trace amount |
|  |  | pH adjuster | Trace amount | Trace amount | Trace amount | Trace amount | Trace amount | Trace amount | Trace amount |
| (C) |  | Purified water | Balance | Balance | Balance | Balance | Balance | Balance | Balance |
| Evaluation |  | Setting power | AA | AA | AA | AA | AA | AA | AA |
|  |  | Quick drying property | A | A | A | A | AA | AA | AA |
|  |  | Natural finish (item 1) | A | A | A | A | AA | AA | AA |
|  |  | Natural finish (item 2) | A | A | A | A | AA | AA | AA |
|  |  | Keeping power | AA | AA | AA | AA | AA | AA | AA |
|  |  | Ease of drawing with pencil after application | AA | AA | AA | AA | AA | AA | AA |
|  |  | Consistency (N) | 0.6 | 0.7 | 0.3 | 0.6 | 0.8 | 1 | 0.7 |

TABLE 4

|  |  |  | Comparative Example 1 | Comparative Example 2 | Comparative Example 3 | Comparative Example 4 | Comparative Example 5 | Comparative Example 6 |
|---|---|---|---|---|---|---|---|---|
| (A) | (A1) | Synthetic smectite-1 | 6 | 6 | — | — | 3 | 5 |
|  |  | Synthetic smectite-2 | — | — | — | — | — | — |
|  | (A2) | Bentonite-1 | — | — | — | — | — | 20 |
| (B) |  | Film-forming polymer emulsion-1 | — | — | — | 1.5 | 1.5 | 1.5 |
|  |  | Film-forming polymer emulsion-2 | — | — | — | — | — | — |
|  |  | Film-forming polymer emulsion-3 | — | — | — | — | — | — |
|  |  | Film-forming polymer emulsion-4 | — | — | — | — | — | — |
|  |  | Film-forming polymer emulsion-5 | 1.5 | — | — | — | — | — |
|  |  | PVP | — | — | 18 | — | — | — |
|  |  | Ethanol | 5 | 5 | 5 | 5 | 5 | 5 |
|  |  | 1,3-Butylene glycol | 3 | 3 | 3 | 3 | 3 | 3 |
|  |  | Preservative | Trace amount | Trace amount | Trace amount | Trace amount | Trace amount | Trace amount |
|  |  | pH adjuster | Trace amount | Trace amount | Trace amount | Trace amount | Trace amount | Trace amount |
| (C) |  | Purified water | Balance | Balance | Balance | Balance | Balance | Balance |
| Evaluation |  | Setting power | C | A | A | C | C | B |
|  |  | Quick drying property | C | AA | C | C | B | A |
|  |  | Natural finish (item 1) | B | AA | C | AA | AA | C |
|  |  | Natural finish (item 2) | B | AA | C | AA | AA | B |

TABLE 4-continued

|  | Comparative Example 1 | Comparative Example 2 | Comparative Example 3 | Comparative Example 4 | Comparative Example 5 | Comparative Example 6 |
|---|---|---|---|---|---|---|
| Keeping power | C | C | A | C | B | B |
| Ease of drawing with pencil after application | B | AA | C | AA | AA | B |
| Consistency (N) | 0.5 | 0.5 | 0 | 0 | 0 | 1.5 |

Example 20: Aqueous Eyebrow Cosmetic with Coloring Material

| Components | Blending ratio (% by mass) |
|---|---|
| 1. Film-forming polymer emulsion-1 | 1.5 |
| 2. Synthetic smectite-1 | 6.0 |
| 3. Black iron oxide | 2.0 |
| 4. Red iron oxide | 2.0 |
| 5. Yellow iron oxide | 1.0 |
| 6. Ethanol | 5.0 |
| 7. 1,3-Butylene glycol | 3.0 |
| 8. Preservative | Trace amount |
| 9. Purified water | Balance |

The details of the components are the same as those already described above.
Production Method
The components 1 to 9 were mixed with a Disper to obtain an aqueous eyebrow cosmetic.
Evaluation
The obtained aqueous eyebrow cosmetic was evaluated in the same manner as described above. The setting power was evaluated as "AA," the quick drying property was evaluated as "AA," the natural finish (item 1) was evaluated as "AA," the natural finish (item 2) was evaluated as "AA," the keeping power was evaluated as "AA," and the ease of drawing with a pencil after application was evaluated as "AA." The consistency of the cosmetic at 25° C. was 0.5 N.

Example 21: Aqueous Eyebrow Cosmetic with Coloring Material

| Components | Blending ratio (% by mass) |
|---|---|
| 1. Film-forming polymer emulsion-1 | 1.5 |
| 2. Synthetic smectite-1 | 5.0 |
| 3. Bentonite-2 | 5.0 |
| 4. Black iron oxide | 2.0 |
| 5. Red iron oxide | 2.0 |
| 6. Yellow iron oxide | 1.0 |
| 7. Ethanol | 5.0 |
| 8. Silica | 3.0 |
| 9. 1,3-Butylene glycol | 3.0 |
| 10. Preservative | Trace amount |
| 11. Purified water | Balance |

The details of the components are the same as those already described above, except for the component shown below.
Bentonite-2: "4444 ALBAGEL PREMIUM NF B. C." (trade name, produced by KUNIMINE INDUSTRIES CO., LTD., bentonite with a viscosity of 240 mPa·s
Production Method
The components 1 to 11 were mixed with a Disper to obtain an aqueous eyebrow cosmetic.
Evaluation
The obtained aqueous eyebrow cosmetic was evaluated in the same manner as described above. The setting power was evaluated as "AA," the quick drying property was evaluated as "AA," the natural finish (item 1) was evaluated as "AA," the natural finish (item 2) was evaluated as "AA," the keeping power was evaluated as "AA," and the ease of drawing with a pencil after application was evaluated as "AA." The consistency of the cosmetic at 25° C. was 0.5 N.

Example 22: Aqueous Eyebrow Cosmetic with Coloring Material

| Components | Blending ratio (% by mass) |
|---|---|
| 1. Film-forming polymer emulsion-1 | 1.5 |
| 2. Bentonite-2 | 18.0 |
| 3. Black iron oxide | 2.0 |
| 4. Red iron oxide | 2.0 |
| 5. Yellow iron oxide | 1.0 |
| 6. Ethanol | 5.0 |
| 7. 1,3-Butylene glycol | 3.0 |
| 8. Preservative | Trace amount |
| 9. Purified water | Balance |

The details of the components are the same as those already described above.
Production Method
The components 1 to 9 were mixed with a Disper to obtain an aqueous eyebrow cosmetic.
Evaluation
The obtained aqueous eyebrow cosmetic was evaluated in the same manner as described above. The setting power was evaluated as "AA," the quick drying property was evaluated as "A," the natural finish (item 1) was evaluated as "A," the natural finish (item 2) was evaluated as "A," the keeping power was evaluated as "AA," and the ease of drawing with a pencil after application was evaluated as "AA." The consistency of the cosmetic at 25° C. was 0.7 N.

Example 23: Aqueous Eyebrow Cosmetic with Coloring Material

| Components | Blending ratio (% by mass) |
|---|---|
| 1. Film-forming polymer emulsion-1 | 1.5 |
| 2. Synthetic smectite-1 | 5.0 |
| 3. Kaolinite | 5.0 |
| 4. Black iron oxide | 2.0 |
| 5. Red iron oxide | 2.0 |
| 6. Yellow iron oxide | 1.0 |
| 7. Ethanol | 5.0 |
| 8. 1,3-Butylene glycol | 3.0 |
| 9. Preservative | Trace amount |
| 10. Purified water | Balance |

The details of the components are the same as those already described above, except for the component shown below.

Kaolinite: "ASP-400" (trade name, produced by BASF SE, kaolinite with a viscosity of 2 mPa·s)

Production Method

The components 1 to 10 were mixed with a Disper to obtain an aqueous eyebrow cosmetic.

Evaluation

The obtained aqueous eyebrow cosmetic was evaluated in the same manner as described above. The setting power was evaluated as "AA," the quick drying property was evaluated as "AA," the natural finish (item 1) was evaluated as "AA," the natural finish (item 2) was evaluated as "AA," the keeping power was evaluated as "AA," and the ease of drawing with a pencil after application was evaluated as "AA." The consistency of the cosmetic at 25° C. was 0.5 N.

What is claimed is:

1. An aqueous eyebrow cosmetic comprising:
   (A) at least one clay mineral selected from the group consisting of synthetic smectite and bentonite;
   (B) an alkyl acrylate copolymer emulsion; and
   (C) water,
   wherein the content of the (A) component is 5.5 to 18% by mass based on the total amount of the aqueous eyebrow cosmetic,
   the (A) component has a viscosity of 1,300 to 25,000 mPa·s as measured at 25° C. when made into a 4% by weight mass aqueous solution,
   the content of the (B) component is 0.3 to 5.0% by mass, in terms of solid content, based on the total amount of the aqueous eyebrow cosmetic,
   the (B) component comprises a polymer having a glass transition temperature of −20° C. or higher,
   the (B) component has an emulsion particle diameter of 20 to 150 nm, and
   the content of the (C) component is 30% by mass or greater based on the total amount of the aqueous eyebrow cosmetic.

2. The aqueous eyebrow cosmetic according to claim 1, wherein the (A) component comprises (A1) the synthetic smectite having a viscosity of 5,000 to 25,000 mPa·s as measured at 25° C. when made into a 4% by weight mass aqueous solution, and
   the content of the (A1) component is 10% by mass or greater based on the total amount of the (A) component.

3. The aqueous eyebrow cosmetic according to claim 1, wherein the mass ratio of the content of the (A) component to the content of the (B) component in terms of solid content is 1.8 or greater.

4. The aqueous eyebrow cosmetic according to claim 1, wherein the (A) component comprises:
   (A1) the synthetic smectite having a viscosity of 5,000 to 25,000 mPa·s as measured at 25° C. when made into a 4% by weight mass aqueous solution; and
   (A2) the bentonite having a viscosity of 1.300 to 5,000 mPa·s as measured at 25° C. when made into a 4% by weight mass aqueous solution.

5. The aqueous eyebrow cosmetic according to claim 4, wherein the blending ratio of the (A1) component to the (A2) component is 1/100 to 100/1.

6. The aqueous eyebrow cosmetic according to claim 4, wherein the mass ratio of the (A1) component to the (A2) component is 1/1 to 10/1.

7. The aqueous eyebrow cosmetic according to claim 1, wherein the (B) component has an emulsion particle diameter of 20 to 130 nm.

8. The aqueous eyebrow cosmetic according to claim 1, wherein the content of the (B) component is 0.4 to 5.0% by mass, in terms of solid content, based on the total amount of the aqueous eyebrow cosmetic.

9. The aqueous eyebrow cosmetic according to claim 1, wherein the aqueous eyebrow cosmetic has a consistency of 0.2 to 1.2 N.

10. The aqueous eye brow cosmetic according to claim 1, wherein the aqueous eye brow cosmetic further comprises an oily component, and the content of the oily component is 5% by mass or less based on the total amount of the aqueous eyebrow cosmetic.

11. The aqueous eye brow cosmetic according to claim 1, wherein the content of the (A) component is 6% to 15% by mass based on the total amount of the aqueous eyebrow cosmetic.

12. The aqueous eye brow cosmetic according to claim 1, wherein the content of the (A) component is 6% to 12% by mass based on the total amount of the aqueous eyebrow cosmetic.

13. The aqueous eye brow cosmetic according to claim 1, wherein the synthetic smectite is at least one selected from the group consisting of synthetic saponite and synthetic stevensite.

14. An eyebrow cosmetic product comprising:
    the aqueous eyebrow cosmetic according to claim 1 housed in a container; and
    an applicator having a coil-shaped or comb-shaped body.

15. An aqueous eyebrow cosmetic consisting of:
    at least one clay mineral selected from the group consisting of synthetic smectite and bentonite;
    at least one coloring material;
    at least one alkyl acrylate copolymer emulsion;
    at least one alcoholic medium;
    water; and
    at least one additive selected from the group consisting of a surfactant, a fiber, a moisturizing agent, a viscosity modifier, a preservative, a pH adjuster, a chelating agent, an ultraviolet ray absorber, a vitamin, a beautifying agent, an antioxidant, and a flavoring agent,
    wherein the at least one clay mineral has a viscosity of 1,300 to 25,000 mPa·s as measured at 25° C. when made into a 4% by weight mass aqueous solution,
    the at least one alkyl acrylate copolymer emulsion comprises a polymer having a glass transition temperature of −20° C. or higher,
    the at least one alkyl acrylate copolymer emulsion has an emulsion particle diameter of 20 to 150 nm,
    the content of the at least one clay material is 5.5 to 18% by mass based on the total amount of the aqueous eyebrow cosmetic,
    the content of the at least one coloring material is less than 1% by mass based on the total amount of the aqueous eyebrow cosmetic,
    the content of the at least one alkyl acrylate copolymer emulsion is 0.3 to 5.0% by mass, in terms of solid content, based on the total amount of the aqueous eyebrow cosmetic, and
    the content of the water is 30% by mass or greater based on the total amount of the aqueous eyebrow cosmetic.

16. The aqueous eye brow cosmetic according to claim 15, wherein the content of the at least one clay material is 6% to 15% by mass based on the total amount of the aqueous eyebrow cosmetic.

17. The aqueous eye brow cosmetic according to claim 15, wherein the content of the at least one clay material is 6% to 12% by mass based on the total amount of the aqueous eyebrow cosmetic.

18. The aqueous eye brow cosmetic according to claim 15, wherein the synthetic smectite is at least one selected from the group consisting of synthetic saponite and synthetic stevensite.

* * * * *